United States Patent [19]

Damaso

[11] Patent Number: 5,080,830

[45] Date of Patent: Jan. 14, 1992

[54] WATER-DISPERSIBLE COMPOSITIONS COMPRISED OF QUATERNARY AMMONIUM COMPOUNDS

[75] Inventor: Gene R. Damaso, Northlake, Ill.

[73] Assignee: Akzo N.V., Netherlands

[21] Appl. No.: 514,989

[22] Filed: Apr. 26, 1990

[51] Int. Cl.$^5$ .................. C11D 1/62; C11D 10/02
[52] U.S. Cl. .................... 252/547; 252/8.8; 252/174.21; 252/174.22; 252/DIG. 13
[58] Field of Search ............ 252/8.8, 8.9, 174.21, 252/547, 174.22, DIG. 13

[56] References Cited

U.S. PATENT DOCUMENTS

| | | | |
|---|---|---|---|
| 4,479,887 | 10/1984 | Seibert et al. | 252/304 |
| 4,521,326 | 6/1985 | Seibert et al. | 252/174.21 |
| 4,675,118 | 6/1987 | Stanley et al. | 252/8.8 |
| 4,704,272 | 11/1987 | Oh et al. | 424/70 |
| 4,741,855 | 5/1988 | Grote et al. | 252/547 |
| 4,885,102 | 12/1989 | Yamamura et al. | 252/8.9 |
| 4,913,828 | 4/1990 | Caswell et al. | 252/547 |

*Primary Examiner*—Paul Lieberman
*Assistant Examiner*—Bradley A. Swope
*Attorney, Agent, or Firm*—David H. Vickrey; Louis A. Morris

[57] ABSTRACT

Water-dispersible compositions of hydrophobic quaternary ammonium compounds and a polyether derivative are disclosed. The compositions may also comprise an alkyl 2-ethylhexyl dimethyl ammonium chloride as a stabilizer. The most preferred composition is comprised of tricetyl methyl ammonium chloride, methoxy polyethylene glycol(17)dodecyl glycol copolymer, and hydrogenated tallow 2-ethylhexyl ammonium chloride. The compositions are useful in aqueous and water-based formulations, and particularly formulations for hair-treating and fabric softening.

17 Claims, No Drawings

WATER-DISPERSIBLE COMPOSITIONS COMPRISED OF QUATERNARY AMMONIUM COMPOUNDS

BACKGROUND OF THE INVENTION

The present invention relates to solid, semi-solid and/or liquid compositions comprised of hydrophobic quaternary ammonium compounds with a dispersing agent and/or a stabilizing agent. The compositions of the instant invention are readily dispersible in water and water-based formulations to provide stable dispersions. Such dispersions are particularly useful in hair-treating formulations, such as shampoos and hair conditioners. Further, the dispersions are also useful as fabric softening agents at any point in the fabric cleaning and drying process (e.g. washing, rinsing or drying cycle, etc.).

As used herein, the term "aqueous dispersion" includes any system having an aqueous continuous phase and a discontinuous phase comprised of a hydrophobic quaternary ammonium compound. Under this definition, the term "aqueous dispersion" includes, as well, "aqueous suspensions" and "aqueous emulsions".

Hydrophobic quaternary ammonium compounds, particularly those derived from certain fatty secondary and tertiary amines, are difficult to disperse in water. Trialiphatic quaternary ammonium compounds are notably difficult to disperse in water. This is especially true of those having relatively long aliphatic chains (e.g., greater than about eight carbon atoms in the aliphatic chains), such as tricetyl methyl ammonium chloride (N-methyl-N,N-dihexadecylhexadecanaminium chloride) and tridodecyl methyl ammonium chloride. Further, once formed, many aqueous dispersions of hydrophobic quaternary ammonium compounds are prone to phase separation. Thus, the formation and the physical stability of many such dispersions are problems.

U.S. Pat. No. 3,325,404 discloses stabilizing in aqueous anionic detergent solutions a cationic softener of the general formula $R_2R'R''N^+X^-$ wherein R is a 14 to 20 carbon atom alkyl radical, R' is a methyl radical and R" is a methyl, ethyl or ethoxylated radical and X is one of several anions. The stabilization is caused by the use of certain monoalkyl quaternary salts having only one 8 to 20 carbon atom alkyl radical chain, the other constituents of the quaternary salt being a 1 to 4 carbon atom alkyl group, a cyclic substituent, benzyl or a benzyl derivative.

U.S. Pat. No. 4,479,887 discloses a polyether derivative of the following general formula

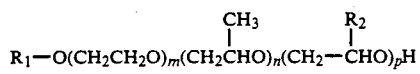

wherein
$R_1$ represents an aliphatic hydrocarbon radical containing 1 to 3 carbon atoms;
$R_2$ represents an aliphatic hydrocarbon radical containing 8 to 30 carbon atoms;
$n = 10 - 50$ (mean value);
$m = 0 - 10$ (mean value);
$p = 1 - 10$ (mean value).

The polyether derivatives are taught to be suitable emulsifiers, particularly in water and oil emulsions. U.S. Pat. No. 4,479,877 discloses use of the polyether derivative in cosmetic emulsions. Mentioned as the oil phase are animal and vegetable oils and fats, synthetic esters of fatty acids with aliphatic alcohols, higher fatty alcohols, waxes, mineral fats and oils such as paraffin oil and vaseline, silicone oils and silicone fats. U.S. Pat. No. 4,479,877 also discloses that its emulsions can be prepared by dissolving the polyether derivatives in the oil phase at about 75° followed by the slow addition of the water phase heated to about 75°.

U.S. Pat. No. 4,650,602 claims an aqueous-alcohol composition comprising at least one oil-soluble perfume oil and 0.3-5 parts by weight of at least one block-copolymeric polyglycol ether of a specific formula (which is within the disclosure of U.S. Pat. No. 4,479,877).

U.S. Pat. Nos. 4,675,118 and 4,569,800 disclose quaternary ammonium salts of the following formula

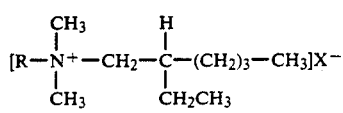

wherein R is an alkyl or alkenyl group having about 6 to about 18 carbon atoms and X is $Cl^-$, $I^-$, $Br^-$ or $OSO_3CH_3^-$.

In U.S. Pat. No. 4,675,118 R is an aliphatic hydrocarbon radical having a carbon chain length of from about 6 to about 18. In U.S. Pat. No. 4,569,800 R is a tallow radical. These quaternary ammonium compounds are said to be useful in fabric softening compounds.

U.S. Pat. Nos. 4,704,272 and 4,728,457 disclose the use of tricetyl methyl ammonium chloride as the hair conditioning agent in shampoo formulations.

There are, however, continuing technical problems with aqueous dispersions and emulsions of hydrophobic quaternary ammonium compounds. Specifically, it is difficult to disperse or emulsify certain quaternary ammonium compounds in water. Additionally, once these compositions are formed they are frequently physically unstable, separating into two or more phases during a reasonable storage time. These problems are overcome by the current invention.

SUMMARY OF THE INVENTION

The invention in one embodiment is a water-dispersible composition comprised of (a) a hydrophobic quaternary ammonium compound and (b) a dispersing agent of the general formula

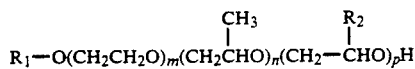

wherein
$R_1$ represents an aliphatic hydrocarbon radical containing 1 to 3 carbon atoms;
$R_2$ represents an aliphatic hydrocarbon radical containing 8 to 30 carbon atoms;
$n = 10 - 50$ (mean value);
$m = 0 - 10$ (mean value); and
$p = 1 - 10$ (mean value).

Such water-dispersible compositions may also contain a stabilizing agent of the general formula

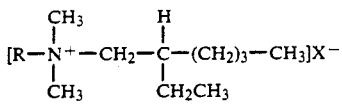

wherein R is an alkyl or alkenyl group having about 6 to about 18 carbon atoms and X. is an anion, for example, $Cl^-$, $I^-$, $Br^-$, $OSO_3H^-$, $OSO_3CH_3^-$ or $SSO_3(CH_2CH_3)^-$. A most preferred R group is a tallow radical.

In another embodiment, the invention is a water-dispersible composition comprised of (a) a hydrophobic quaternary ammonium compound, (b) a dispersing agent, and (c) a stabilizing agent of the general formula

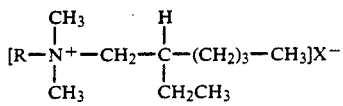

wherein R is an alkyl or alkenyl group having about 6 to about 18 carbon atoms and $X^-$ is an anion, for example, $Cl^-$, $I^-$, $Br^-$, $OSO_3H^-$, $OSO_3CH_3^-$ or $OSO_3(CH_2CH_3)$.

In its most preferred embodiment, the current invention is a water-dispersible composition comprised of tricetyl methyl ammonium chloride as a hydrophobic quaternary ammonium compound, methoxypolyethyleneglycol(17) dodecyl glycol copolymer as a dispersing agent and hydrogenated tallow 2-ethylhexyl dimethyl ammonium chloride as a stabilizing agent.

The water-dispersible compositions of the current invention are particularly useful in hair-treating formulations and in fabric softening compositions.

DETAILED DESCRIPTION OF THE INVENTION

The water-dispersible compositions of the current invention are comprised of hydrophobic quaternary ammonium compounds with a dispersing agent and/or a stabilizing agent. The instant compositions are designed to overcome the problems of dispersing and stabilizing hydrophobic quaternary ammonium compounds in aqueous media. The water-dispersible compositions of this invention are particularly useful in water-based hair-treating formulations and in fabric-treating compositions. For water-dispersible compositions intended for hair-care formulations or fabric-treating compositions, a typical weight ratio of quaternary ammonium compound to dispersing agent is about 1:1 to about 5:1 and a typical weight ratio of quaternary ammonium compound to stabilizing agent is about 1:1 to about 5:1.

Quaternary Ammonium Compounds. The quaternary ammonium compounds of the current invention are those which are difficult to disperse in water. Such quaternary ammonium compounds may be described as "hydrophobic". The preferred hydrophobic quaternary ammonium compounds in the current invention are quaternary ammonium salts of the following general formula

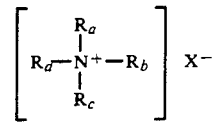

wherein $R_a$ is a $C_8$ to $C_{22}$ alkyl or alkenyl radical, $R_b$ is a $C_8$ to $C_{22}$ alkyl or alkenyl radical, $R_c$ is a $C_8$ to $C_{22}$ alkyl or alkenyl radical, $R_d$ is a $C_1$ to $C_7$ alkyl or alkenyl radical and X in an anion.

In its most preferred embodiment, the hydrophobic quaternary ammonium salt of the current invention is tricetyl methyl ammonium chloride (available from Akzo Chemicals Inc., Chicago, Ill. under the trade name Arquad ®316).

For personal care, and especially hair-treatment uses, such as shampooing and conditioning, a typical concentration of quaternary ammonium compound in aqueous formulations of the current invention is about 8 to about 35 wt.%.

Dispersing Agent. The preferred dispersing agents of the current invention are of the class described in U.S. Pat. No. 4,479,887. Broadly, U.S. Pat. No. 4,479,887 describes polyether derivatives of the following general formula:

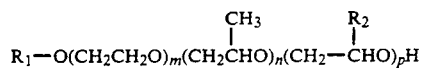

wherein
$R_1$ represents an aliphatic hydrocarbon radical containing 1 to 3 carbon atoms;
$R_2$ represents an aliphatic hydrocarbon radical containing 8 to 30 carbon atoms;
$n = 10-50$ (mean value);
$m = 0-10$ (mean value); and
$p = 1-10$ (mean value).

The preferred polyether derivative for use as an emulsifier in the current invention is methoxy(polyethylene glycol-17)dodecyl glycol copolymer (available from Akzo Chemicals Inc., Chicago, Ill. under the trade name Elfacos ®O/W 100).

Effective amounts of the dispersing agent in aqueous formulations of the current invention are typically about 6 to about 12 wt.% of the aqueous dispersion.

Stabilizing Agent. The stabilizing agents useful in the current invention are disclosed in U.S. Pat. Nos. 4,675,118 and 4,569,800. These stabilizing agents are quaternary ammonium salts of the following general formula

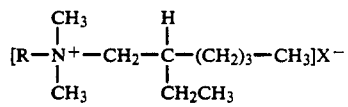

wherein R is an alkyl or alkenyl group having about 6 to about 18 carbon atoms and $X^-$ is $Cl^-$, $I^-$, $Br^-$, $OSO_3H^-$, $OSO_3CH_3^-$ or $OSO_3(CH_2CH_3)^-$.

The preferred stabilizing agent of the current invention is hydrogenated tallow 2-ethylhexyl dimethyl ammonium chloride (available from Akzo Chemicals Inc., Chicago, Illinois under the trade name Arquad ®HTL-8).

An effective amount of stabilizer for the current aqueous formulations has been found to be in the range of about 8 to about 15 wt.% of the aqueous formulation.

The current invention is further illustrated by following non-limiting examples.

COMPARATIVE EXAMPLE A

In several separate tests, tricetyl methyl ammonium chloride (Arquad ®316) varying in activity from 2% to 30% (2.2 to 33.3 wt.%) was melted at 70° C. and added to 80° C. water with agitation in attempts to form a dispersion or an emulsion. It was not possible to form aqueous dispersions of tricetyl methyl ammonium chloride having an activity greater than 2%. The 2% active tricetyl methyl ammonium chloride dispersion separated on standing after one day.

EXAMPLE 1

Tricetyl methyl ammonium chloride (Arquad ®316), 2% active (2.2 wt.%), was blended with 0.5 wt.% methoxy (PEG-17) dodecyl glycol copolymer (Elfacos-®O/W 100) to form a water-dispersible composition. The composition was heated to 70° C. and was easily dispersed in water at 70° C. with agitation. The resulting dispersion was allowed to stand at 45° C. The dispersion was stable for two weeks, after which it separated into two phases.

EXAMPLE 2

The three components listed below were melted at 70° C. to form a blend.

| | |
|---|---|
| Tricetyl methyl ammonium chloride (Arquad ® 316) (30% active) | 33.3 wt. % |
| Methoxy (PEG-17) dodecyl glycol copolymer (Elfacos ® O/W 100) | 8.4 wt. % |
| Hydrogenated tallow 2-ethylhexyl dimethyl ammonium chloride (Arquad ® HTL-8) (92%) | 9.0 wt. % |

The resulting blend was added with agitation to 49.3 wt.% soft water which had been heated to 70° C. then cooled to room temperature to produce a semi-solid composition. A dispersion of water and 6.67 wt.% of the semi-solid composition was formed by heating the composition to 60° C. and adding it with agitation to soft water. The resulting dispersion was storage stable (that is, maintained a single phase) over a period of 7 months at a temperature of 45° C.

The foregoing examples have been presented to provide an enabling disclosure of the current invention and to illustrate its surprising superiority in view of known technology. Such examples are not intended to unduly restrict the scope and spirit of the following claims.

I claim:

1. A water-dispersible composition comprised of
   (a) about 8 to about 35 wt.% hydrophobic quaternary ammonium compound of the general formula

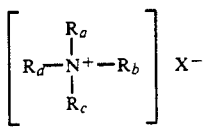

wherein $R_a$ is a $C_8$ to $C_{22}$ alkyl or alkenyl radical,
$R_b$ is a $C_8$ to $C_{22}$ alkyl or alkenyl radical,
$R_c$ is a $C_8$ to $C_{22}$ alkyl or alkenyl radical,
$R_d$ is a $C_1$ to $C_7$ alkyl or alkenyl radical and X is an anion, and (b) a dispersing agent of the general formula

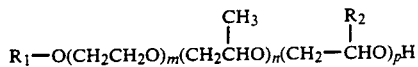

wherein
$R_1$ represents an aliphatic hydrocarbon radical containing 1 to 3 carbon atoms;
$R_2$ represents an aliphatic hydrocarbon radical containing 8 to 30 carbon atoms;
$m = 10-50$ (mean value);
$n = 0-10$ (mean value); $p = 1-10$ (mean value); and (c) a stabilizing agent of the general formula

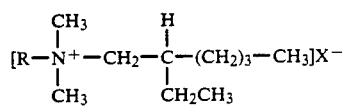

wherein R is an alkyl or alkenyl group having 6 to 22 carbon atoms and X is an anion, wherein the weight ratio of (a):(b) is 1:1 to 5:1 and the weight ratio of (a):(c) is 1:1 to 5:1.

2. A water-dispersible composition of claim 1 wherein the hydrophobic quaternary ammonium compound is tricetyl methyl ammonium chloride.

3. A water-dispersible composition of claim 1 wherein R is an alkyl group having 14 to 18 carbon atoms.

4. A water-dispersible composition of claim 1 wherein R is a hydrogenated tallow radical.

5. An aqueous dispersion of a hydrophobic quaternary ammonium compound, said dispersion comprising
   (a) about 8 to about 35 wt.% hydrophobic quaternary ammonium compound of the general formula

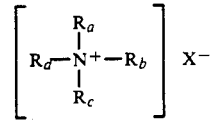

wherein $R_a$ is a $C_8$ to $C_{22}$ alkyl or alkenyl radical,
$R_b$ is a $C_8$ to $C_{22}$ alkyl or alkenyl radical,
$R_c$ is a $C_8$ to $C_{22}$ alkyl or alkenyl radical,
$R_d$ is a $C_1$ to $C_7$ alkyl or alkenyl radical and X is an anion, (b) about 6 to about 12 wt.% dispersing agent of the general formula

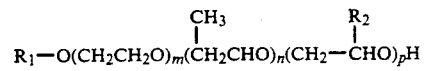

wherein
R represents an aliphatic hydrocarbon radical containing 1 to 3 carbon atoms;
R represents an aliphatic hydrocarbon radical containing 8 to 30 carbon atoms;
$m = 10-50$ (mean value);
$n = 0-10$ (mean value);
$p = 1-10$ (mean value);

(c) about 8 to about 15 wt.% stabilizing agent of the general formula

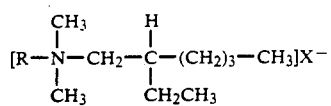

wherein R is an alkyl group having about 6 to about 18 carbon atoms and X is an anion, and
(d) water.

6. An aqueous dispersion of claim 5 wherein R is a hydrogenated tallow radical.

7. An aqueous dispersion of claim 5 wherein the hydrophobic quaternary ammonium compound is tricetyl methyl ammonium chloride.

8. A hair conditioner or shampoo comprised of the aqueous dispersion of claim 5.

9. An aqueous dispersion comprised of the water-dispersible composition of claim 1.

10. An aqueous dispersion comprised of the water-dispersible composition of claim 5.

11. A fabric softening formulation comprised of the water-dispersible composition of claim 1.

12. A fabric softening formulation comprised of the water-dispersible composition of claim 5.

13. A water-dispersible composition of claim 1 wherein the dispersing agent is methoxy polyethylene glycol (17) dodecyl glycol copolymer.

14. An aqueous dispersion of claim 5 wherein the dispersing agent is methoxy polyethylene glycol (17) dodecyl glycol copolymer.

15. An aqueous disperion of claim 5 wherein the weight ratio of (a):(b) is about 1:1 to about 5:1.

16. An aqueous dispersion of claim 5 wherein the weight ratio of (a):(c) is about 1:1 to about 5:1.

17. A hair conditioner or shampoo comprised of the water-dispersible composition of claim 1.

* * * * *